(12) United States Patent
Duong

(10) Patent No.: US 12,071,603 B2
(45) Date of Patent: Aug. 27, 2024

(54) DEVICE FOR EXPOSING AN ALGAL SOLUTION TO LIGHT, ASSOCIATED PHOTOBIOREACTOR AND IMPLEMENTATION METHOD

(71) Applicant: SUEZ GROUPE, Paris la Defense (FR)

(72) Inventor: Frédéric Duong, Pezilla-la-Riviere (FR)

(73) Assignee: SUEZ INTERNATIONAL, Paris la Défense (FR)

( * ) Notice: Subject to any disclaimer, the term of this patent is extended or adjusted under 35 U.S.C. 154(b) by 208 days.

(21) Appl. No.: 16/337,033

(22) PCT Filed: Sep. 26, 2017

(86) PCT No.: PCT/EP2017/074385
§ 371 (c)(1),
(2) Date: Mar. 27, 2019

(87) PCT Pub. No.: WO2018/060197
PCT Pub. Date: Apr. 5, 2018

(65) Prior Publication Data
US 2020/0032181 A1  Jan. 30, 2020

(30) Foreign Application Priority Data

Sep. 27, 2016 (FR) .................................. 1659114

(51) Int. Cl.
*C12M 1/00* (2006.01)
*C12M 1/09* (2006.01)

(52) U.S. Cl.
CPC ............ *C12M 21/02* (2013.01); *C12M 23/56* (2013.01); *C12M 31/08* (2013.01)

(58) Field of Classification Search
USPC ........................................................ 435/292.1
See application file for complete search history.

(56) References Cited

U.S. PATENT DOCUMENTS

| 4,868,123 A | * | 9/1989 | Berson | ................... C12M 23/06 |
| | | | | 435/286.2 |
| 5,029,879 A | * | 7/1991 | Strang, Sr. | ............ F16L 41/088 |
| | | | | 277/606 |

(Continued)

FOREIGN PATENT DOCUMENTS

| CN | 101636484 A | 1/2010 |
| CN | 102037118 A | 4/2011 |

(Continued)

OTHER PUBLICATIONS

Miya et al., "Appts. for incubating photosynthetic microbes—comprises light collector having Fresnel lens and/or reflection mirror, and optical guides to radiate collected light into incubating tank", Database WPI, Week 199316 XP002770092.

(Continued)

*Primary Examiner* — Holly Kipouros
*Assistant Examiner* — Nathan G Esperon
(74) *Attorney, Agent, or Firm* — NIXON & VANDERHYE

(57) ABSTRACT

Disclosed is a device for exposing an algal solution to light, for a photobioreactor, this exposure device including a flat support including at least one opening capable of holding at least one shaft, the shaft being made of a liquid-tight, translucent or even transparent flexible material, and including an open end capable of holding a sleeve, the sleeve being translucent, or even transparent, and arranged to seal and attach the shaft to the support. The exposure device has positive floatability in water. Also disclosed is a photobioreactor equipped with such a device and a start-up method for such a photobioreactor.

18 Claims, 2 Drawing Sheets

(56) References Cited

U.S. PATENT DOCUMENTS

| | | | | |
|---|---|---|---|---|
| 8,479,441 | B2* | 7/2013 | Williamson | A01G 33/00 47/1.4 |
| 8,481,304 | B2* | 7/2013 | Woerlee | C12M 31/08 359/228 |
| 2003/0059932 | A1* | 3/2003 | Craigie | C12M 21/02 47/1.4 |
| 2008/0178739 | A1* | 7/2008 | Lewnard | C12M 21/02 435/257.1 |
| 2009/0320362 | A1* | 12/2009 | Williamson | C12M 31/08 47/60 |
| 2017/0342361 | A1 | 11/2017 | Barbarin | |

FOREIGN PATENT DOCUMENTS

| | | | |
|---|---|---|---|
| CN | 102296035 | * | 12/2011 |
| CN | 102307985 A | | 1/2012 |
| CN | 103614285 | * | 3/2014 |
| CN | 105209593 A | | 12/2015 |
| CN | 205576121 U | | 9/2016 |
| DE | 103 15 750 A1 | | 10/2004 |
| JP | H05-64578 A | | 3/1993 |
| KR | 20130108735 | * | 10/2013 |
| KR | 20160102728 | * | 8/2016 ............ C12M 21/02 |
| KR | 20160102729 | * | 8/2016 |
| WO | WO-2009018498 A2 | * | 2/2009 ............ C12M 21/02 |
| WO | 2009/051479 A2 | | 4/2009 |
| WO | 2010/064780 A1 | | 6/2010 |
| WO | 2010/077638 A1 | | 7/2010 |
| WO | WO-2010077638 A1 | * | 7/2010 ............ C12M 21/02 |
| WO | 2013/011448 A1 | | 1/2013 |
| WO | WO-2013011448 A1 | * | 1/2013 ............ C12M 21/02 |
| WO | 2016/087779 A1 | | 6/2016 |

OTHER PUBLICATIONS

International Search Report, dated Dec. 20, 2017, from corresponding PCT application No. PCT/EP2017/074385.

Office Action issued in Chinese Patent Application No. 201780059255.7 dated Mar. 3, 2022.

* cited by examiner

DEVICE FOR EXPOSING AN ALGAL SOLUTION TO LIGHT, ASSOCIATED PHOTOBIOREACTOR AND IMPLEMENTATION METHOD

BACKGROUND OF THE INVENTION

Field of the Invention

The present invention relates to the field of the production of concentrated algal solutions and in particular concerns a device for exposing an algal solution to light. The invention also has for subject matter a photobioreactor integrating this kind of exposure device as well as a method of starting up this kind of photobioreactor.

Algal culture, in particular microalgal culture for producing a photosynthetic biofuel or nutraceutic compounds from algal biomass, can only be developed on a large scale by significantly reducing the cost of the photobioreactors and operating them. Moreover, algal production is not reserved to warm and sunny regions alone, and it is necessary to envisage technical solutions enabling algal production to be increased in countries situated at the latitudes of temperate regions.

Description of the Related Art

There are known in the prior art photobioreactors that use compartments of different shapes, separated by rigid walls, in particular made of polycarbonate or other monomer or polymer materials. Thus the document DE 103 15 750 shows a photobioreactor including rows of rigid transparent vertical tubes in which flows the algal solution subjected to luminous radiation that passes through the tubes, which enables photosynthesis. However, these materials are costly and the fabrication time is long for components intended for industrial applications of photobioreactors that can cover several tens of hectares. Moreover, these materials are inflammable and their ecological footprint is significant for both manufacture and disposal.

There are also known above ground photobioreactors that necessitate a high financial investment and are of a height that induces a windage that penalizes construction. Because of their large area in contact with the external air, above ground photobioreactors are very sensitive to climatic conditions, which affects their performance in cold, windy or too hot regions.

There is also known from the prior art document WO2013011448A1 a light exposure device based on very thin flexible tubes that assume a cylindrical shape only because of a static pressure difference between the liquid internal to the tubes and the liquid of the pool in which the microalgae are cultivated. The flexible nature of the tubes submerged in the culture pool enables a cylindrical shape to be imparted to them exclusively because of the height difference between the internal liquid and the water level of the pool. The static pressure is therefore uniform over all the height of the tubes without any mechanical stress, which makes it possible to reduce the thickness of the tubes whilst maintaining good mechanical strength. This type of solution makes it possible to envisage compact photobioreactors made using extremely lightweight and low cost materials.

They may be used in existing natural or artificial pools suitable for the continuous culture of microalgae. Regular spacing of the sleeves is obtained by a perforated plate mounted on a fixed supporting structure above the pool.

However, the fixing of this supporting structure is often critical because of the culture area and the liquid charge contained in the tubes.

Moreover, mounting and fixing this supporting structure over a pool filled with water is subject to constraints linked to handling and using the multitude of tubes and accessories necessary for culture to take place.

This is why one object of the invention is to avoid the constraints imposed by the supporting structure and in particular to simplify assembling it and fixing it over the pool.

SUMMARY OF THE INVENTION

To this end, the invention proposes a device for exposing an algal solution to light, for a photobioreactor, adapted to be used by floating it in a pool subject to the combination of and the equilibrium between Archimedes' principle and Torricelli's principle.

To be more precise, the invention proposes a device for exposing an algal solution to light, for a photobioreactor, that exposure device comprising a flat support comprising at least one opening capable of receiving at least one tube, the tube being made of a flexible, liquid-tight and translucent, or even transparent, material and comprising an open end able to receive a sleeve, the sleeve being translucent, or even transparent, and adapted to block said tube and to fix it to the support, characterized in that the exposure device has positive buoyancy in water, in the sense that the real weight of the flat support and the non-submerged parts of the tubes is less than the Archimedean upthrust induced when it is submerged.

Optional, complementary or substitute features of the invention are stated hereinafter.

The exposure device may comprise at least one buoyancy buoy or a floating structure disposed underneath said support in such a manner as to define a free space between said support and the level of the algal solution.

The flat support may have positive buoyancy in water, in the sense that the real weight of the flat support and the non-submerged parts of the tubes is less than the Archimedean upthrust induced when it is submerged.

The support may be a framework constituted of a material the specific gravity of which is less than 2, preferably less than 1.

The support may be a perforated plate constituted of a material the specific gravity of which is less than 2, preferably less than 1.

The sleeve may include an optical concentrator adapted to concentrate light toward the interior of the at least one tube.

The sleeve may include a valve for the admission of a liquid into the tube.

The exposure device may further include mooring and/or anchoring means.

The invention also has for subject matter a photobioreactor for the production of an algal solution, comprising a pool and at least one light exposure device, that light exposure device including a support comprising at least one opening capable of receiving at least one tube, the tube being made of a flexible, liquid-tight and translucent, or even transparent, material and comprising an open end able to receive a sleeve, the sleeve being translucent, or even transparent, and adapted to block said tube and to fix it to the support, characterized in that the at least one exposure device is a light exposure device according to any one of the embodiments of the invention.

Optional, complementary or substitute features of the invention are stated hereinafter.

The photobioreactor may comprise a plurality of exposure devices assembled together in such a manner as to increase the area of exposure of the algal solution to light.

The photobioreactor may further comprise an aspiration means adapted to aspirate the liquid contained in the at least one tube.

The photobioreactor may further comprise a device for replacing "the at least one tube", that replacement device comprising a drum and being adapted to wind "the at least one tube" onto the drum and/or to unwind "the at least one tube" from that drum.

The photobioreactor may comprise in the lower part of the pool means for distribution of a pressurized gas, in particular carbon dioxide mixed or not with air, that agitates the algal solution.

The photobioreactor may further comprise orientable reflectors disposed at the periphery of said photobioreactor in such a manner as to increase the capture area and the intensity of the light rays, notably when the azimuth and the angle of the sun's rays are low.

The invention also has for subject matter a method of using a photobioreactor according to any one of the embodiments of the invention, characterized in that it comprises successively:

a step of assembling at least one light exposure device,
a step of installing at least one exposure device in the empty pool of the photobioreactor,
a step of filling the pool with a liquid for the production of an algal solution.

Optional, complementary or substitute features of the invention are stated hereinafter.

The method may further comprise, after filling the pool, a step of filling the at least one tube of the at least one exposure device with a liquid that is neutral for the algal solution in order not to degrade the algal solution in the event of accidental rupture of the tube.

After the step of filling the at least one tube and when the at least one tube is submerged in the algal solution, the height of liquid in the tubes may be greater than that of the algal solution in order to provide a differential hydrostatic pressure for maintaining the shape of the tube without stress.

The method may further comprise, after filling the at least one tube, a step of mooring and/or anchoring the at least one exposure device.

The method may further comprise, after filling the pool, a step of seeding the liquid with a strain of microalgae to produce an algal solution.

BRIEF DESCRIPTION OF THE DRAWINGS

Other advantages and particular features of the invention will become apparent on reading the detailed description of nonlimiting uses and embodiments and from the following appended drawings.

DESCRIPTION OF THE PREFERRED EMBODIMENTS

For clarity and conciseness, the references in the figures correspond to the same elements.

The embodiments described hereinafter being in no way limiting on the invention, there could in particular be considered variants of the invention comprising only a selection of the features described, separately from the other features described (even if that selection is isolated within a sentence comprising those other features), if that selection of features is sufficient to confer a technical advantage or to distinguish the invention from the prior art. This selection comprises at least one feature, preferably functional with no structural details, or with only some of the structural details if those alone are sufficient to confer a technical advantage or to distinguish the invention from the prior art.

Figure 1:
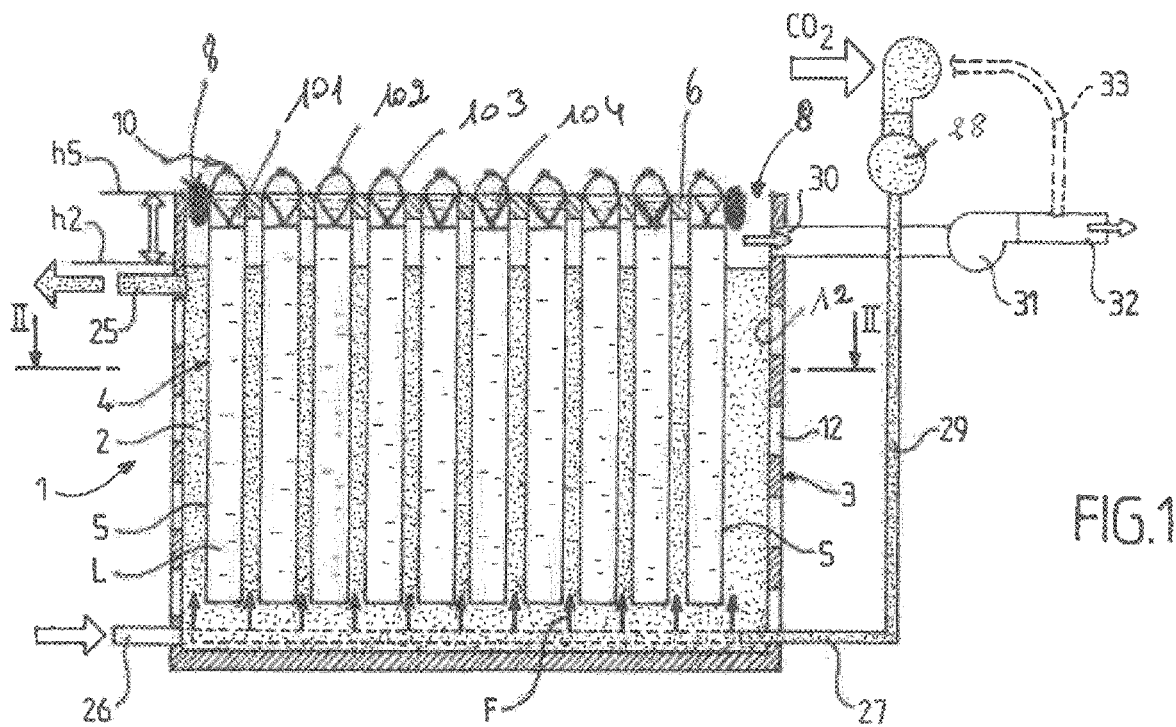
FIG. 1 is a diagrammatic vertical section of a photobioreactor according to the invention with a pool containing the algal solution.

Referring to FIG. 1 of the drawings, there can be seen a photobioreactor 1, designated by the abbreviation PBR, for the production of a concentrated algal solution 2. The PBR includes a pool 3 containing the algal solution and a device for exposing that algal solution to light.

According to the invention, the exposure device comprises at least one supporting structure or one flat support 6, comprising at least one opening, at least one flexible material tube 5 that is liquid-tight and translucent, or even transparent, and comprises an open end able to receive a sleeve 10, the sleeve being translucent, or even transparent, and adapted to block said tube and fix it to the support.

By translucent it is meant that the tube 5 and the sleeve 10 are adapted to allow light rays to pass through them, said rays making possible photosynthesis reactions in the pool.

By transparent is meant that the tube 5 and the sleeve 10 are adapted to allow light rays to pass through them (transmission of light by refraction). It is moreover possible to see clearly through the tube 5 and the sleeve 10.

Still in accordance with the invention, the light exposure device has positive buoyancy in water. By "positive buoyancy in water" is meant that the real weight of the light exposure device is less than the Archimedean upthrust, which enables the light exposure device to remain at the surface of the pool, and thus to float.

It is advantageously the entire light exposure device associated with the non-submerged parts of the tubes filled with water that has positive buoyancy.

As described in more detail next, buoyancy may be provided in different ways.

According to a first embodiment, the light exposure device may comprise one or more flotation buoys 8 attached under the support 6 so that it can float and can be held above the surface of the filled pool.

According to a second embodiment, the supporting structure or support 6 has intrinsic positive buoyancy and may be a framework 61 constituted of a material the specific gravity of which is less than 2, preferably less than 1. That framework may then consist in an assembly of marine grade particle board or any other rot-proof composite material of low specific gravity, such as polyurethane, polystyrene charged with glass fibers.

According to a third embodiment, the supporting structure or support 6 has intrinsic positive buoyancy and may be a perforated plate 62 also constituted of a material the specific gravity of which is less than 2, preferably less than 1. The material may also be marine grade particle board or any other rot-proof composite material of low specific gravity, such as polyurethane, polystyrene charged with glass fibers.

Of course, the light exposure device may provide a supporting structure or support 6 constituted of a material the specific gravity of which is less than 2, preferably less than 1, and additionally provide one or more flotation buoys 8.

Also in detail, the tube 5 is made from a transparent flexible material, preferably one that is resistant to traction. This tube 5 is suspended from the supporting structure or support 6 and is filled with a liquid L that imparts a cylindrical shape to this tube.

The flexible tube 5 is advantageously made from an ultraviolet-resistant material, in particular of polyurethane terephthalate or like material. The tube may be produced by rolling up a rectangular portion of sheet 4 and assembling the two parallel edges by gluing or welding or impulse. The lower end of the tube is closed whereas the upper end remains open to be fixed, at its periphery, to the support 6.

Figure 3:
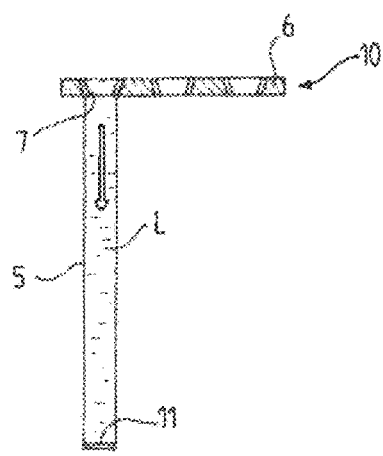
FIG. 3 is a diagram to a larger scale of a vertical flexible tube mounted on its supporting structure.

The tube 5 may be fixed to the support 6 as shown in FIG. 3 by providing, in the support 6, a frustoconical opening 7 for each tube of reducing section from top to bottom. The upper edge of the tube 5 is wedged between the frustoconical wall of the opening 7 by a sleeve 10 that is itself frustoconical, conjugate with the opening 7, and made of transparent material.

Figure 6:
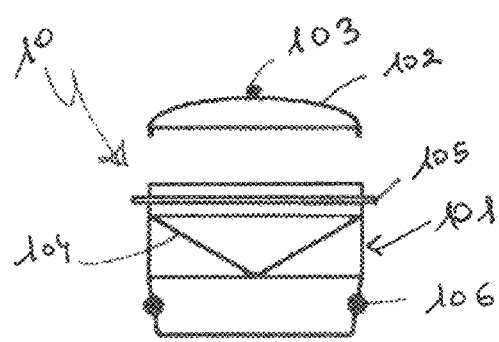
FIG. 6 is a diagrammatic section of a component for fixing a flexible tube to its supporting structure.
Figure 7:
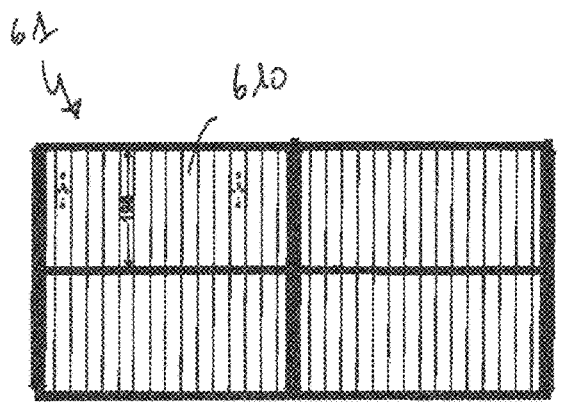
FIG. 7 is a plan view of a first embodiment of the structure supporting the flexible tubes.
Figure 8:
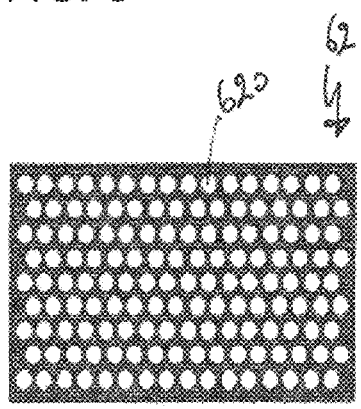
FIG. 8 is a top view of a second embodiment of the structure supporting the flexible tubes.

The tubes 5 may also be fixed to the support 6 in a different manner, in particular by flanges or an O-ring 106 as shown in FIG. 6, instead of being retained by nested conical parts. It is not necessary to provide a total seal at the level of this fixing because there is no contact between the algal solution and the water situated inside the submerged tubes 5.

A rib 105 may be provided around the exterior surface of the sleeve to prevent the sleeve passing through the opening 610, 620 of the support when mounting the tube 5 on said support.

When the supporting structure is a framework 61, the tubes are inserted between the bars 610 and immobilized by means of their sleeve also inserted between the bars 610 with a tight fit.

When the supporting structure is a perforated plate 62, the tubes are inserted in the holes 620 and immobilized by means of their sleeve also inserted in the holes 620 with a tight fit.

The perforated plate may be transparent and thin. It may also be reinforced by a transparent reinforcement that provides sufficient surface stiffness to support a point load (cleaning, maintenance).

There may be provided on either side of the perforated plate a gutter that enables collection of rainwater. The natural flow slope could be provided by a pressure difference in inflatable spacers.

According to the embodiment from FIG. 1, the pool 3 is filled with algal solution 2. A plurality of flexible transparent tubes 5 filled with liquid L are submerged in the algal solution 2 and are regularly distributed to transmit and to diffuse light captured at the upper end of the tubes 5 throughout the pool and the solution 2.

According to this embodiment, the liquid L that fills the tubes 5 has the main function of transmitting and diffusing the captured light and is constituted in particular of water and an additive (the additive may be antifreeze, a fluorescent or antiseptic product or an anti-foaming product). The closed lower end of the tubes 5 is preferably equipped with a ballast 11. This ballast 11 makes it possible to prevent the empty tubes floating when they are introduced into the algal solution 2, which would make it difficult to fill them subsequently with water. The ballast may take the form of a rod or a heavy ball of metal or mineral material.

The composition of the liquid L that fills the tubes 5 is neutral relative to the algal solution in order to avoid all risk in the event of accidental rupture. In the embodiment from FIG. 1 the liquid L is essentially water, possibly with an additive, and that additive may be antifreeze, an antiseptic or a fluorescent product.

The height h5 of the liquid in the tubes 5 is slightly greater than that h2 (FIG. 1) of the algal solution in the pool in order to produce a differential hydrostatic pressure (h5-h2) that maintains the cylindrical shape without stress on the flexible wall of the tubes 5. The height of the sleeve support at the level of the algal solution is the result of the equilibrium between the Archimedean upthrust and the weight carried by the perforated plates and the non-submerged part of the tubes.

The tubes are advantageously filled with water up to the sleeve 10. This enables the speed of propagation of light in the tube to occur essentially in water with no transmission discontinuity. That transmission then has the same quality as fiber optic transmission.

Likewise, not leaving air in the tube makes it possible to prevent the formation of mist on the internal surface of the walls, which could form a barrier to light.

The exterior walls of the tubes 5 are in contact with the algal solution 2 that fills the pool.

In order to optimize the "light well" character of the tube, it is advantageous to add to the sleeve an optical concentrator 104 to concentrate light toward the interior of the tube. Thus an increase of brightness is obtained inside the tubes 5. To this end, and as shown in FIG. 6, the sleeve 10 may include a body 101 holding a Fresnel lens 104. The sleeve may be closed in sealed manner by a translucent, or even transparent, cover 102 that may also include an optical concentrator.

The sleeve may advantageously include a valve 103 for admitting the liquid into the tube when filling the tube with a neutral liquid. This valve is then preferably on the cover 102 of the tube.

Figure 9:
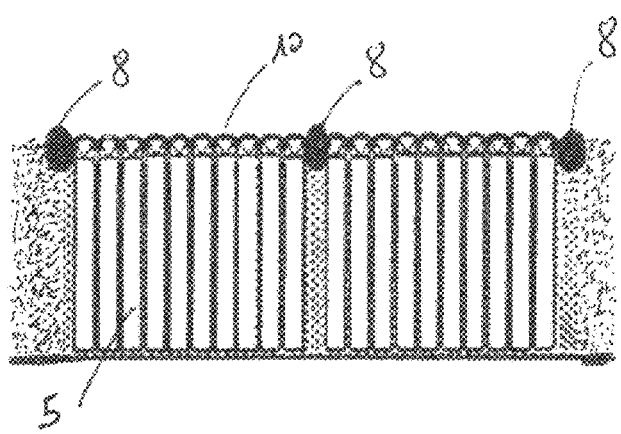
FIG. 9 is a diagrammatic vertical section of a third embodiment of the structure supporting the flexible tubes.

As shown in FIG. 9, the pool 3 may include a plurality of light exposure devices according to the invention interconnected by means of buoys 8.

Complementary inflatable floats spaced regularly and transversely to the main structure may then be provided. They then make it possible to support a high point load (snow or maintenance tools) without remanent deformation of the surface. The light exposure device may advantageously further include mooring and/or anchoring means (not shown in the figures). In fact, because of the positive buoyancy of the device, it is not necessary to fix it to the surface of the pool of the PBR as was necessary in the prior art. If it is required to position the light exposure device at a precise location of the pool, or if there is a plurality of light exposure devices that could collide, it is therefore desirable either to moor them to a fixed point outside the pool or to anchor them to the bottom of the pool.

Figure 2:
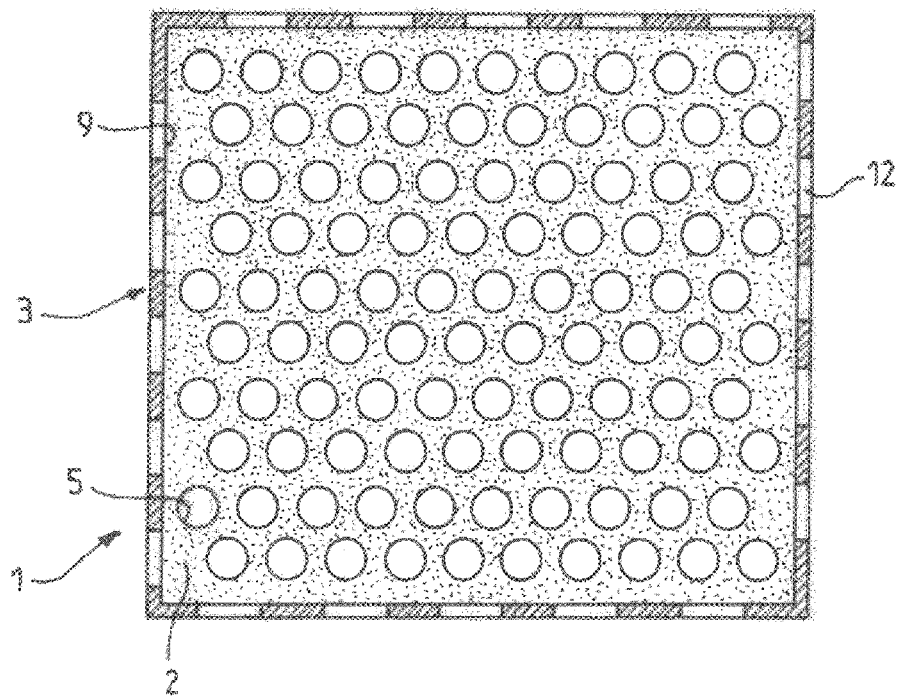
FIG. 2 is a horizontal section taken along the line II-II in FIG. 1.

The pool may be of square or rectangular shape as shown in FIG. 2 or of cylindrical shape with a circular cross section (not shown). The pool may be above ground as shown in FIG. 1 in which case portholes 12 may be provided in the walls to complete the exposure to light of the algal solution 2. The pool 3 may also be partly underground or entirely underground. The pool may equally be made from elements prefabricated in a factory and assembled on site with a sealing covering (liner) of the type used in swimming pools.

Figure 4:
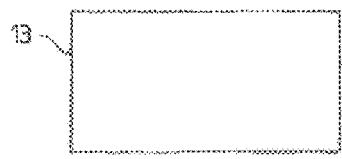
FIGS. 4 and 5 are vertical cross sections to a smaller scale of possible shapes for the pool of the photobioreactor.
Figure 5:
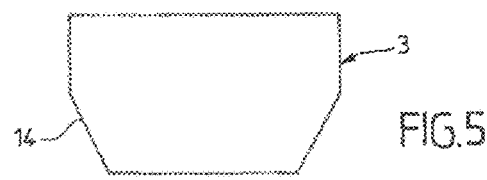

The vertical cross section 13 of the pool may be rectangular, as shown in FIG. 4, with a flat roof. The vertical section 14 may alternatively have a lower part of trapezoidal shape as shown in FIG. 5.

In the case of an above ground or partly underground pool, the walls may also be made of transparent liquid-tight, in particular flexible, membrane corresponding to the exposure of the algal solution to light.

A pipe 25 for extraction of the algal solution is provided in the upper part of the pool, in order to benefit from the higher concentration of algae. After extraction and filtering, the water is returned into the lower part via a pipe 26. The nutrients for the development of the algae may be injected into the returned water.

The process of extraction of the biomass in the algal solution from the photobioreactors is continuous and, because it therefore does not necessitate intermediate storage in tanks, it is not necessary to provide ultrafiltration using membranes to prevent the unwanted development of algae in the tanks.

In order to optimize the photosynthesis reactions, the photobioreactor according to the invention may provide a system for filtering wavelengths of light.

Still with this objective, the photobioreactor may also provide sunshades to reduce the luminous intensity of the rays incident on the surface of the pool. The material of the external lenses may be colored or photochromic to limit the luminous intensity captured.

Likewise, the photobioreactor may also provide artificial lighting means such as light-emitting diodes.

In such a manner as to increase the incident radiation capture area and also in such a manner as to increase the luminous intensity when the azimuth and the angle of the suns rays are low, the photobioreactor may further comprise orientable reflectors disposed at the periphery of said photobioreactor.

The photobioreactor according to the invention may provide means for draining a tube in order to replace it and install another tube.

It is possible to drain the pool without demounting the tubes, in which case the tubes will form a multitude of "posts" stiffened by significantly increasing the static pressure inside them and in the lower part of the tubes.

The tube that is wished to be removed is connected at its upper end to a pipe plugged into the inlet of means for aspirating the liquid inside the tube. The aspiration means is generally constituted of a pump. The external pressure exerted by the algal solution compresses the sleeve, which is flattened and which, after disconnecting the aspiration pipe, is removed from the pool.

A winding device for replacing the tubes is provided above the pool. This device comprises a rotary winding drum mounted to be mobile in translation above the cells of the pool (for example on a mobile gantry), whilst being supported by a rail or a gutter. Cleaning members, notably rotary brushes, are provided to move in translation with the drum and to determine a vertical passage interstice for the flattened tube which is cleaned by these brushes when it is removed from the algal solution. The device enables unwinding of a flattened new tube to be placed in the algal solution to replace that which has been removed.

The PBR includes, in the lower part of the pool, means for distribution of a compressed gas, in particular carbon dioxide ($CO_2$) mixed or not with air, encouraging the development of the algae and agitating the algal solution. The distribution means are constituted of manifolds enabling blowing of the gas, as shown by the arrows F, into the spaces between the tubes 5. The distribution means 27 are connected to the outlet of a rotary piston or screw compressor 28 by a pipe 29. The distribution of carbon dioxide ($CO_2$) agitates and homogenizes the algal solution in the pool 9.

The fact that the device that carries the tubes floats at a distance from the surface of the pool (because of buoys that raise the device, for example) allows the gases to escape easily.

It is possible to capture and to recycle some of the gases that escape from the upper part of the pool in order better to exhaust the carbon dioxide ($CO_2$). To this end the PBR further includes gas capture means 30 formed by a pipe opening in the upper part of the pool 9, above the algal solution, in the gaseous atmosphere above that solution. These capture means are connected to the suction side of a fan 31 that discharges the gases into a pipe 32, notably leading to the atmosphere. Some of these gases may be recycled thanks to an offtake 33 on the pipe 32 connected to the suction side of the compressor 28.

The pool 3 is thermally insulated in order to reduce heat losses. The temperature of the algal solution is advantageously regulated by means (not shown) for heating and/or cooling the water introduced via the pipe 26 into the pool after filtration, which makes it possible to maintain optimum conditions for growth of the algae and microalgae.

Of known heating devices there may be cited heated floors fed with hot water at low and medium temperature, bubbling through with saturated sludge or combustion gases charged with $CO_2$, plate, tube or spiral type external heat exchangers, submerged or self-regulated external electrical heating elements.

Complementary thermal insulation equipment may be used with double walls for the tube supports.

Concerning now the method of starting up a photobioreactor according to the invention, it is firstly necessary to assemble at least one light exposure device. This assembly is preferably carried out in dry dock in the pool, but may also be carried out outside the pool. Once assembly has been carried out, i.e. once the tubes are inserted in their support by means of their sleeve, it is necessary to position one or more light exposure devices at the bottom of the empty pool of the photobioreactor. It then suffices to fill the pool with a liquid for the production of an algal solution. In other words, when the whole device has been assembled, launching it enables the structure of the PBR to rise progressively as the pool is filled with water until its operational level is reached.

After filling the pool, the tubes may be filled straight away with a liquid that is neutral for the algal solution, so as not to degrade the algal solution in the event of accidental rupture of the tube.

When the tubes are submerged in the algal solution, the height ($h5$) of liquid in the tubes is advantageously greater than that ($h2$) of the algal solution in order to ensure a differential hydrostatic pressure for maintaining the shape of the tube without stress.

Thus the cylindrical and vertical shape of the flexible tubes is maintained by the differential static pressure between the liquid inside the tubes and the liquid in the pool the level of which is slightly lower than that of the tubes (this relates to Torricelli's principle). This pressure difference is constant over all the height of the tubes, whatever their submerged height. This considerably limits internal pressure stresses on the flexible material of the tubes.

The submerged height of the tubes is in fact linked to the Archimedean upthrust that is exerted on the floating structure of the tube support. This upward force produces the difference in level between the liquid in the tubes and the top level of the pool. To summarize, it is the combination of and the equilibrium between Archimedes principle and Torricelli's principle that enable retention of the tubes.

In order to stabilize all of the light exposure devices, the exposure devices may be moored and/or anchored together or at the periphery of the pool.

Finally, there may be carried out a step of seeding the liquid with a strain of microalgae to produce an algal solution.

It will be noted that the benefit of the buoyancy of the light exposure device is very particularly expressed in the use of a photobioreactor according to any of the embodiments described above.

In fact, with the prior art devices it was necessary to fix the support firmly to the ground around the pool and then to mount the elements one by one over the pool. The assembly, installation and operation of the elements above the pool was then problematic and necessitated appropriate transportation and lifting machinery (for example mounted on a barge). Moreover, personnel safety weighed heavily on the timing and the infrastructures. Should some of the equipment fall into the pool, operation was commensurately delayed.

The floating nature of the light exposure device therefore makes it possible to simplify the use of the light exposure device and to make it secure at lower cost.

It is also to be noted that the buoyancy of the light exposure devices enables great modularity of design. In fact, given that it is not necessary to fix them at the periphery of the pool, it is possible to add them, to remove them or to change them while the pool is operating.

In other words, these light exposure devices are highly autonomous in terms of use (installation, service life).

Moreover, the position of the tubes of the light exposure device relative to the surface of the water is always the same regardless of variations in the water level in the pool.

No supporting structure with feet placed on the ground is necessary.

It is possible to assemble the light exposure device away from the pool and to move it in translation over the pool whether filled or not.

There is only a slight risk of damage linked to a modification of the water level in the pool.

Assembly is rapid and does not necessitate heavy lifting means.

The overall dimensions of a device of this kind when dismantled conform to the road haulage loading gauge, i.e. to a maximum overall size of 2.5 m.

It is possible to use recycled materials for the structure and the floats.

Of course, the invention is not limited to the examples that have just been described and numerous modifications may be made to those examples without departing from the scope of the invention. Moreover, the various features, shapes, variants and embodiments of the invention may be associated with one another in diverse combinations provided that they are not mutually exclusive or incompatible.

The invention claimed is:

1. An open photobioreactor for the open-circuit production of an algal solution, comprising:
    a pool filled with the algal solution;
    at least one tube; and
    at least one flat perforated plate comprising at least one opening capable of receiving the at least one tube,
    wherein the at least one perforated plate has positive buoyancy in water and floats on a surface of the algal solution in the pool,
    wherein the at least one perforated plate is not rigidly fixed to a periphery, surface, or ground of the pool and is not rigidly mounted over the pool, but instead floats on the surface of the algal solution at a distance from at least one edge of the pool,
    wherein a gutter is provided on either side of the at least one perforated plate to enable collection of rainwater,
    wherein the at least one tube is made of a flexible, liquid-tight, and translucent or transparent material and comprises an open end able to receive a sleeve,
    wherein the sleeve is translucent or transparent and comprises a cover configured to block the at least one tube, and a flange, o-ring, or rib to fix the at least one tube to the at least one flat perforated plate,
    wherein the at least one tube is partially submerged in the algal solution and is filled with a liquid that is neutral for the algal solution in order not to degrade the algal solution in the event of accidental rupture of the at least one tube, and
    wherein a height of the liquid in the at least one tube is greater than a height of the algal solution in the pool in order to provide a differential hydrostatic pressure for maintaining the shape of the at least one tube without stress.

2. The photobioreactor as claimed in claim 1, further comprising a plurality of perforated plates assembled together in such a manner as to increase the area of exposure of the algal solution to light.

3. The photobioreactor as claimed in claim 1, further comprising an aspiration means adapted to aspirate the liquid contained in the at least one tube.

4. The photobioreactor as claimed in claim 1, further comprising a device for replacement of the at least one tube, the device for replacement comprising a drum and being adapted to wind the at least one tube onto the drum and/or to unwind the at least one tube from that drum.

5. The photobioreactor as claimed in claim 1, further comprising in a lower part of the pool means for distribution of a pressurized gas that agitates the algal solution.

6. The photobioreactor as claimed in claim 1, further comprising orientable reflectors disposed at a periphery of said photobioreactor in such a manner as to increase a capture area and an intensity of light rays.

7. The photobioreactor as claimed in claim 1, wherein the at least one flat perforated plate is a framework constituted of a material a specific gravity of which is less than 1.

8. The photobioreactor as claimed in claim 1, wherein the at least one flat perforated plate has positive buoyancy in water, in a sense that a real weight of the at least one flat perforated plate is less than an Archimedean upthrust induced when it is submerged.

9. The photobioreactor as claimed in claim 1, wherein the at least one flat perforated plate is a framework constituted of a material a specific gravity of which is less than 2.

10. The photobioreactor as claimed in claim 1, wherein the at least one flat perforated plate is constituted of a material a specific gravity of which is less than 1.

11. The photobioreactor as claimed in claim 1, wherein the at least one sleeve includes an optical concentrator adapted to concentrate light toward the interior of the at least one tube.

12. The photobioreactor as claimed in claim 1, wherein the at least one sleeve includes a valve for the admission of a liquid into the at least one tube.

13. The photobioreactor as claimed in claim 1, wherein the at least one flat perforated plate includes a mooring and/or an anchor.

14. The photobioreactor as claimed in claim 1, wherein the at least one flat perforated plate comprises at least one buoyancy buoy disposed underneath in such a manner as to define a free space between said plate and a level of the algal solution.

15. A method of using the photobioreactor of claim 1, comprising successively:
   assembling the at least one tube with the at least one flat perforated plate, and
   installing the at least one tube and the at least one plate in the pool filled with the algal solution.

16. The method of claim 15 further comprising filling the at least one tube with the liquid that is neutral for the algal solution in order not to degrade the algal solution in the event of accidental rupture of the at least one tube.

17. The method of claim 16 further comprising submerging the at least one tube in the algal solution wherein, when the at least one tube is submerged in the algal solution, the height of the liquid that is neutral for the algal solution in the at least one tube is greater than the height of the algal solution in order to provide a differential hydrostatic pressure for maintaining the shape of the tube without stress.

18. The method of claim 16 further comprising, after filling the at least one tube, a step of mooring and/or anchoring the at least one flat perforated plate.

\* \* \* \* \*